United States Patent [19]
Uchimiya et al.

[11] Patent Number: 5,986,172
[45] Date of Patent: Nov. 16, 1999

[54] RICE NADH-DEPENDENT REDUCTASE, GENE THEREFOR, AND USE THEREOF

[75] Inventors: Hirofumi Uchimiya, Kawasaki; Takaomi Fushimi, Shiraoka-machi; Ume Kudou, Shiraoka-machi; Michito Tagawa, Shiraoka-machi, all of Japan

[73] Assignee: Nissan Chemical Industries, Ltd., Tokyo, Japan

[21] Appl. No.: 09/068,109

[22] PCT Filed: Dec. 22, 1995

[86] PCT No.: PCT/JP95/02641

§ 371 Date: Jul. 17, 1998

§ 102(e) Date: Jul. 17, 1998

[87] PCT Pub. No.: WO97/23627

PCT Pub. Date: Jul. 3, 1997

[51] Int. Cl.⁶ .............................. A01H 5/00; C12N 15/29; C12N 15/82; C12N 15/70

[52] U.S. Cl. .......................... 800/279; 800/278; 800/301; 800/320.2; 800/305; 800/315; 800/316; 800/317.2; 800/317.3; 800/317.4; 800/320; 800/320.1; 800/320.3; 435/418; 435/419; 435/468; 435/320.1; 435/69.1; 435/71.1; 435/252.33; 536/23.6

[58] Field of Search ................................ 435/69.1, 320.1, 435/410, 419, 468, 418, 71.1, 252.33; 536/23.6; 800/278, 279, 295, 298, 301, 320.2, 305, 315, 316, 317.2, 317.3, 317.4, 320, 320.1, 320.3

[56] References Cited

PUBLICATIONS

Lebrun et al, Phytochem., vol. 27, pp. 77–84, 1988.
Nakasako et al, Biochem., vol. 37, pp. 9931–9939, 1998.
Howard et al, Annu. Rev. Microbiol., vol. 50, pp. 491–512, 1996.
Greenler et al, Plant Mo. Biol., vol. 13, pp. 139–150, 1989.
Broglie et al, Science, vol. 254, pp. 1194–1197, 1991.
Gurmukh S. Johal et al, "Reductase Activity Encoded by the HM1 Disease Resistance Gene in Maize", Science, vol. 258, pp. 985–987, Nov. 6, 1992.
Ann Depicker et al, "Frequencies of simultaneous transformation with different T–DNAs and their relevance to the Agrobacterium/plant cell interaction", Mol. Gen. Genet., vol. 201, pp. 477–484, 1985.
Kinya Toriyama et al, "Transgenic Rice Plants After Direct Gene Transfer Into Protoplasts", Bio/Technology, vol. 6, pp. 1072–1074, Sep. 1988.
Hirofumi Uchimiya et al, "Random sequencing of cDNA–libraries reveals a variety of expressed genes in cultured cells of rice (Oryza sativa L.)", The Plant Journal, vol. 2, No. 6, pp. 1005–1009, 1992.
Hubert Guilley et al, "Transcription of Cauliflower Mosaic Virus DNA: Detection of Promoter Sequences, and Characterization of Transcripts", Cell, vol. 30, pp. 763–773, Oct. 1982.

*Primary Examiner*—David T. Fox
*Assistant Examiner*—Ashwin Mehta
*Attorney, Agent, or Firm*—Oblon, Spivak, McClelland, Maier & Neustadt, P.C.

[57] ABSTRACT

The present invention relates to a rice NADH-dependent reductase gene or variant thereof, to a rice NADH-dependent reductase or analog thereof, to DNA or expression vector comprising the gene or variant thereof and capable of expressing it in microorganism or plant cells, and to a plant or seeds thereof transformed with said expression vector.

According to the present invention, plants can be protected from damages caused by plant pathogenic microorganisms by applying the transformed plant to its cultivation.

14 Claims, 1 Drawing Sheet

Figure 1

SEQUENCE LISTING

<160> NUMBER OF SEQ ID NOS: 6

<210> SEQ ID NO 1
<211> LENGTH: 1272
<212> TYPE: DNA
<213> ORGANISM: Oryza sativa, cell type: anther
<220> FEATURE:
<221> NAME/KEY: CDS
<222> LOCATION: (10)..(1101)
<223> OTHER INFORMATION: Identification Method: P

<400> SEQUENCE: 1

```
gcggcggca atg gcg gaa gag ggg agg agc ggc ggc gtc gcc gga gac ggc      51
          Met Ala Glu Glu Gly Arg Ser Gly Gly Val Ala Gly Asp Gly
            1               5                  10

Ygtc cgg gtg tgc gtc acc gga ggc gcc ggc ttc atc gcc tcg tgg ctc       99
Val Arg Val Cys Val Thr Gly Gly Ala Gly Phe Ile Ala Ser Trp Leu
 15                  20                  25                  30 gtg aag aag ctc ctc gag aga ggc tgc atc gtc cat gcc acg ctg cga      147
Val Lys Lys Leu Leu Glu Arg Gly Cys Ile Val His Ala Thr Leu Arg
                 35                  40                  45 acg atg gga gat gag gag aag gcc ggg ctg ctc cgg cgg ctc gtc cac      195
Thr Met Gly Asp Glu Glu Lys Ala Gly Leu Leu Arg Arg Leu Val His
             50                  55                  60 ggc gcg gcg gag cgg ctg cgg ctg ttc gag gcc gat ctc ttc gac gcc      243
Gly Ala Ala Glu Arg Leu Arg Leu Phe Glu Ala Asp Leu Phe Asp Ala
         65                  70                  75 gcc acc ttc ggg ccg gcg atc gcc ggc tgc cag ttc gtc ttc ctc atc      291
Ala Thr Phe Gly Pro Ala Ile Ala Gly Cys Gln Phe Val Phe Leu Ile
     80                  85                  90 gcc acg ccg tac ggg ctg gag gcc tcc aac tcc aag tac aag aac acg      339
Ala Thr Pro Tyr Gly Leu Glu Ala Ser Asn Ser Lys Tyr Lys Asn Thr
 95                 100                 105                 110 gcg gat gcg gca gtg gac gcg gtg cgc gag atc ctc cgg caa tgc gcg      387
Ala Asp Ala Ala Val Asp Ala Val Arg Glu Ile Leu Arg Gln Cys Ala
                115                 120                 125 gaa tcc aag acg gtg aag cgc gtc atc cac acc gcc tcg ata tcc acc      435
Glu Ser Lys Thr Val Lys Arg Val Ile His Thr Ala Ser Ile Ser Thr
            130                 135                 140 gcc tcg ccg ttg atc gac gtc ccc ggc gcc ggc gtc ggc gcc gcc ggg      483
Ala Ser Pro Leu Ile Asp Val Pro Gly Ala Gly Val Gly Ala Ala Gly
        145                 150                 155 tac agg gac ttc atc gac gag tcc tgc tgg act ccg ctc gac gtc gac      531
Tyr Arg Asp Phe Ile Asp Glu Ser Cys Trp Thr Pro Leu Asp Val Asp
    160                 165                 170
```

-continued

| | | |
|---|---|---|
| tac cca ctc cgg agc gcc cac ttc gac aag tac gtg ctg tcg aag atg<br>Tyr Pro Leu Arg Ser Ala His Phe Asp Lys Tyr Val Leu Ser Lys Met<br>175                    180                185              190 | 579 |
| atg tcg gag aag gag ctc ctg ggc tac aac gac gga gag ggc cgg gag<br>Met Ser Glu Lys Glu Leu Leu Gly Tyr Asn Asp Gly Glu Gly Arg Glu<br>            195                200                205 | 627 |
| ttc gag gtg gtc acc ctg ctg tgc ggc ctc gtg gcc ggc gac acg gtc<br>Phe Glu Val Val Thr Leu Leu Cys Gly Leu Val Ala Gly Asp Thr Val<br>210                    215                220 | 675 |
| ctc ggc cgc gcc ccg gag acg ctg gag tac gcc gtg tcg ccg gtg tcc<br>Leu Gly Arg Ala Pro Glu Thr Leu Glu Tyr Ala Val Ser Pro Val Ser<br>        225                230                235 | 723 |
| cgg aac gag ccg tcc ttc ggg ttc ctg agg ctg ctg cag agg ctg gtc<br>Arg Asn Glu Pro Ser Phe Gly Phe Leu Arg Leu Leu Gln Arg Leu Val<br>240                    245                250 | 771 |
| ggg tcg gtg ccg ctg gtg cac gcc gac gac gtc tgc gac gcg ctc gtc<br>Gly Ser Val Pro Leu Val His Ala Asp Asp Val Cys Asp Ala Leu Val<br>255                    260                265              270 | 819 |
| ttc tgc atg gat cag ccg tcg ctc gcc ggc cgc ttc ctc tgc tcc gcc<br>Phe Cys Met Asp Gln Pro Ser Leu Ala Gly Arg Phe Leu Cys Ser Ala<br>            275                280                285 | 867 |
| gcc tac ccg acc atc cac gac atc gtc gaa cac ttc gcc gcc aag tac<br>Ala Tyr Pro Thr Ile His Asp Ile Val Glu His Phe Ala Ala Lys Tyr<br>290                    295                300 | 915 |
| cct cac ctc gac gtc ctc aaa gag ccg gag agg gag gtg gcg agg gtg<br>Pro His Leu Asp Val Leu Lys Glu Pro Glu Arg Glu Val Ala Arg Val<br>        305                310                315 | 963 |
| cag ccg gcg gca gac aag ctg ggt gag ctg ggc ttc agg tac aag tac<br>Gln Pro Ala Ala Asp Lys Leu Gly Glu Leu Gly Phe Arg Tyr Lys Tyr<br>320                    325                330 | 1011 |
| ggc atg gag gag ata ctc gac ggc agc gtc ggc tgc gcg gcg agg ctg<br>Gly Met Glu Glu Ile Leu Asp Gly Ser Val Gly Cys Ala Ala Arg Leu<br>335                    340                345              350 | 1059 |
| ggt tac atc gac gca gcc aag ctc agg ccg cag gaa gga tga<br>Gly Tyr Ile Asp Ala Ala Lys Leu Arg Pro Gln Glu Gly<br>                355                360 | 1101 |
| atctgctaca gatttgcagg atgaagaaga tggatgatat tgttcggtt ttgaacaagt | 1161 |
| ttttggtgtt tgtttgtaat ctcatgtgtt ctgaatacct ctctcatgta tcacatgacg | 1221 |
| catttctgcg tcagagaacg atattaataa gtactccgtg gagctcgcta a | 1272 |

<210> SEQ ID NO 2
<211> LENGTH: 363
<212> TYPE: PRT
<213> ORGANISM: Oryza sativa, cell type: anther

<400> SEQUENCE: 2

Met Ala Glu Glu Gly Arg Ser Gly Gly Val Ala Gly Asp Gly Val Arg
1               5                  10                  15

Val Cys Val Thr Gly Gly Ala Gly Phe Ile Ala Ser Trp Leu Val Lys
                20                  25                  30

Lys Leu Leu Glu Arg Gly Cys Ile Val His Ala Thr Leu Arg Thr Met
        35                  40                  45

Gly Asp Glu Glu Lys Ala Gly Leu Leu Arg Arg Leu Val His Gly Ala
    50                  55                  60

Ala Glu Arg Leu Arg Leu Phe Glu Ala Asp Leu Phe Asp Ala Ala Thr
65                  70                  75                  80

Phe Gly Pro Ala Ile Ala Gly Cys Gln Phe Val Phe Leu Ile Ala Thr
                85                  90                  95

```
Pro Tyr Gly Leu Glu Ala Ser Asn Ser Lys Tyr Lys Asn Thr Ala Asp
            100                 105                 110

Ala Ala Val Asp Ala Val Arg Glu Ile Leu Arg Gln Cys Ala Glu Ser
        115                 120                 125

Lys Thr Val Lys Arg Val Ile His Thr Ala Ser Ile Ser Thr Ala Ser
    130                 135                 140

Pro Leu Ile Asp Val Pro Gly Ala Gly Val Gly Ala Ala Gly Tyr Arg
145                 150                 155                 160

Asp Phe Ile Asp Glu Ser Cys Trp Thr Pro Leu Asp Val Asp Tyr Pro
                165                 170                 175

Leu Arg Ser Ala His Phe Asp Lys Tyr Val Leu Ser Lys Met Met Ser
            180                 185                 190

Glu Lys Glu Leu Leu Gly Tyr Asn Asp Gly Gly Arg Glu Phe Glu
        195                 200                 205

Val Val Thr Leu Leu Cys Gly Leu Val Ala Gly Asp Thr Val Leu Gly
    210                 215                 220

Arg Ala Pro Glu Thr Leu Glu Tyr Ala Val Ser Pro Val Ser Arg Asn
225                 230                 235                 240

Glu Pro Ser Phe Gly Phe Leu Arg Leu Leu Gln Arg Leu Val Gly Ser
                245                 250                 255

Val Pro Leu Val His Ala Asp Val Cys Asp Ala Leu Val Phe Cys
            260                 265                 270

Met Asp Gln Pro Ser Leu Ala Gly Arg Phe Leu Cys Ser Ala Ala Tyr
        275                 280                 285

Pro Thr Ile His Asp Ile Val Glu His Phe Ala Ala Lys Tyr Pro His
    290                 295                 300

Leu Asp Val Leu Lys Glu Pro Gly Arg Glu Val Ala Arg Val Gln Pro
305                 310                 315                 320

Ala Ala Asp Lys Leu Gly Glu Leu Gly Phe Arg Tyr Lys Tyr Gly Met
                325                 330                 335

Glu Glu Ile Leu Asp Gly Ser Val Gly Cys Ala Ala Arg Leu Gly Tyr
            340                 345                 350

Ile Asp Ala Ala Lys Leu Arg Pro Gln Glu Gly
        355                 360

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Synthetic
      Oligomer

<400> SEQUENCE: 3
agtacggggt tggtgctctc gc                                              22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Synthetic
      Oligomer

<400> SEQUENCE: 4
atctccactg acgtaaggga tgac                                            24

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Artificial Sequence:Synthetic
      Oligomer

<400> SEQUENCE: 5
tcatcgcaag accggcaaca g                                              21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic
      Oligomer

<400> SEQUENCE: 6
ccgggagttc gaggtggtca                                                20
```

RICE NADH-DEPENDENT REDUCTASE, GENE THEREFOR, AND USE THEREOF

FIELD OF THE INVENTION

The present invention relates to a recombinant rice NADH-dependent reductase which can be used in breeding techniques in order to give a resistance to plant pathogenic microorganisms by gene transfer into plants including rice, and to a gene encoding the reductase. It also relates to a plant transformed with an expression vector containing the above mentioned gene, and to a seed thereof.

BACKGROUND OF THE INVENTION

In cultivation of rice, pathogenic microorganisms of plant diseases such as blast have caused problems of decline of the yield and have been controlled mainly by chemicals. The chemical control is generally effective only immediately before the diseases occur but much less effective after the diseases occur, thereby causing serious damages. On the other hand, genetic analyses have shown that various disease-resistant genes might exist on the basis of their chromosome maps (Proteins, Nucleic Acids, Enzymes, vol. 37 (7) 1353 (1992)). It is importantly desirable in rice breeding to introduce the trait of a variety having such a disease-resistant gene, i.e. resistant gene, into cultivated rice plants through the cross-breeding.

Although a number of such resistant genes were presumed to exist in rice plants and were associated with one another on chromosome maps, there were no reports revealing that these genes were isolated and clarified at genetic level.

Some successes have been reported in conferring a resistance to pathogenic microorganisms to plants other than rice, e.g. by introducing both genes of chitinase and β-1,3-glucanase into tobacco plants or the like (M. B. Sela-Buurllage et al., Plant Physiol., 101, 857 (1993)), or introducing a detoxification enzyme gene for toxin produced by tobacco wildfire bacteria into tobacco plants (V. Nikolaeva et al., In vitro, 29A, 3, Pt. 2, 87A (1993)). In maize, a gene for an enzyme which reduces and detoxifies HC toxin (*Helminthosporium carbonum* toxin) produced by its pathogen *Cochliobolus carbonum*, i.e. HC toxin reductase, was isolated and proved to be consistent with the resistant locus of the chromosome (G. S. Johal et al., Science, 258, 985 (1992)).

In rice, disease-resistant genes such as genes for chitinase (KIM et al., Biosci. Biotechnol. Biochem. 58 (6) 1164 (1894)), lipoxygenase (JP-A-6-225774), phytoalexin synthetase (Minami et al., Eur. J. Biochem. 185, 19 (1989)), and peroxidase (Ito et al., Plant Cell Report, 13, 361 (1994)) were isolated, but there were no reports evidencing any correlation between these genes and disease resistances. Studies on the resistance mechanism of rice infection with a blast pathogen suggested two mechanisms, one being a mechanism of inhibiting the growth of pathogenic microorganisms by hypersensitive cell death in infected parts of rice plant cells at early infection phase and the other being a mechanism of inhibiting infection by alteration of cell membranes (S. ARASE, Chemistry and Biology, vol. 31 (4), 235 (1993)), but the gene responsible for the disease resistance has not yet been clarified.

Thus, the occurrence of plant diseases, as well as the resistance to plant diseases, has been studied in rice with difficulty and without progress at genetic level, because both the pathogenic infection mechanism and the resistance expression mechanism in plants are very complex and because any correlation could not be obtained even between labo-level resistance and field-level resistance.

However, several disease-resistant genes have been believed to be involved in various resistance mechanisms. Therefore, it will be necessary to isolate a full-length gene resistant to rice diseases including blast; to clarify the structure of the isolated gene as well as the primary structure of the corresponding protein; to express the gene in rice plants; and to examine functions of the gene in detail.

In this context, we have now isolated a gene for NADH-dependent reductase having an ability to detoxify a toxin produced by a pathogen of blast as one of disease-resistance genes, analyzed its structure, and introduced it into plants, thereby finding that the disease resistance could readily be given to plants such as rice. Namely, while keeping in mind the report that the protein expressed from a gene encoding a protein presumed to be the HC toxin reductase isolated from maize as described above offers a resistance by reducing and detoxifying the HC toxin produced by the pathogenic *Cochliobolus carbonum,* we have now succeeded in isolation of a cDNA clone having a partial sequence highly homologous to the HC toxin reductase gene by the random sequencing of cDNA from a rice anther cDNA library; and in isolation of a full-length rice NADH-dependent reductase cDNA from rice anthers using the obtained cDNA clone as a probe. As a result, it has been evidenced that this gene was associated with the blast-resistant locus.

SUMMARY OF THE INVENTION

The present invention provides an isolated rice NADH-dependent reductase gene comprising a base sequence encoding the 1–363 amino acid sequence shown in SEQ ID NO:1 or a variant thereof encoding an analog protein containing addition, deletion and/or substitution in the amino acid sequence and having the enzyme activity of the NADH-dependent reductase.

According to one embodiment of the present invention, the base sequence is from the nucleotide numbered 10 to the nucleotide numbered 1098 shown in SEQ ID NO:1.

The present invention also provides an isolated rice NADH-dependent reductase having the 1–363 amino acid sequence shown in SEQ ID NO:1, or an analog thereof containing addition, deletion and/or substitution in the amino acid sequence and having the enzyme activity. The protein shown in SEQ ID NO:1 is listed as SEQ ID NO:2 in the Sequence Listing.

The present invention also provides DNA comprising the rice NADH-dependent reductase gene or a variant thereof and capable of being expressed in microorganism or plant cells such as *Escherichia coli, Bacillus subtilis,* and yeasts.

The present invention further provides an expression vector capable of expressing the rice NADH-dependent reductase gene or a variant thereof in microorganism or plant cells such as *Escherichia coli, Bacillus subtilis,* and yeasts.

The present invention still further provides a plant transformed with the expression vector.

The present invention still yet further provides a method for protecting the plant against damages caused by plant pathogenic microorganisms, preferably *Pyricularia oryzae,* by applying the plant to its cultivation.

BRIEF DESCRIPTION OF THE DRAWING

FIG. 1 shows a construction scheme of the expression vector pUYK1 containing the rice NADH-dependent reductase gene YK1.

DETAILED DESCRIPTION OF THE INVENTION

The present invention will be described in detail below. The DNA sequence encoding the rice NADH-dependent reductase of the present invention comprises a single open reading frame as shown particularly in SEQ ID No:1 of the SEQUENCE LISTING described later. It is likely that this open reading frame contains a full length because its 5' end starts with ATG at nucleotide numbers 10 to 12 and contains a non-translational region of 9 bases at a site upstream thereof, and its 3' end terminates with TGA at nucleotide numbers 1099 to 1101 and contains a sequence TAATAA presumed as a poly(A) addition signal at a site downstream thereof. It can also be said that the base sequence of this isolated cDNA comprises a full-length base sequence encoding the rice NADH-dependent reductase because it contains the base sequence of a probe cDNA fragment prepared from a cDNA library derived from rice anthers and it is highly homologous with the already determined maize base sequence (G. S. Johal et al., supra) in the NADH-binding region and downstream thereof.

The amino acid sequence deduced from this base sequence is shown in parallel in SEQ ID NO:1. The protein presumed from the amino acid sequence consists of 363 amino acid residues and has a presumed molecular weight of 39234 daltons. Comparison between the deduced amino acid sequence of the protein and the amino acid sequence of the known HC toxin reductase derived from maize indicated that their homology was 73% and that their NADH-binding regions were concerved.

It should be noted that this NADH-dependent reductase gene is identified at the Pi-i locus that is presumed to be a blast-resistant gene by means of the gene mapping; namely, the newly isolated NADH-dependent reductase expresses a resistance to blast when it is expressed in rice plants through the mechanism of reducing a toxic compound produced by the blast pathogen or a toxic compound responsible for endogenous resistance in rice. It was not quite expectable that the NADH-dependent reductase of the present invention had a high homology with the HC toxin reductase derived from maize at amino acid level and that it might be responsible for diseases of completely different plants from maize despite of such a high homology.

Thus, the DNA sequence of the present invention can be characterized by the primary amino acid sequence of rice NADH-dependent reductase and functional properties thereof.

The present invention includes a rice NADH-dependent reductase protein having the 1–363 amino acid sequence shown in SEQ ID NO:1 or analogs thereof containing a modification such as addition, deletion and/or substitution in the amino acid sequence and having the enzyme activity. In this sequence, the enzyme activity is not affected even if the amino acid residue Met at position 1 is absent. The modification includes both a spontaneous mutation due to differences in classes of rice plants, in fields for cultivation, etc., and an artificial mutation for modification to obtain, e.g. higher enzyme activity or higher stability than naturally derived.

It is generally known that proteins are substituted, added or deleted due to accidental alterations of natural gene sequences encoding them, and lots of examples are known in which altered proteins maintain a similar activity to that of the original proteins. Twenty amino acids are classified into several groups and any alteration of amino acids belonging to the same group is said to influence the structure or activity of a protein in a similar manner. For example, the aromatic residues consisting of phenylalanine, tyrosine and tryptophan form a group in view of the similarity of amino acid residues actually observed, and they are said to have the same functions. Another group consists of positively charged residues lysine, arginine and histidine, and still another group consists of negatively charged residues glutamic acid and aspartic acid. Other group consists of aliphatic non-polar residues valine, leucine and isoleucine and also includes slightly polar residues methionine and cysteine. In view of the size of side chain, on the other hand, a group consists of residues having small side chains including serine, threonine, aspartic acid, asparagine, glycine, alanine, glutamic acid, glutamine and proline. Among these amino acids, substitution practically occurs during evolution of proteins under natural conditions. The substitution, addition or deletion of amino acids shown herein can be artificially modified by using the site-directed mutagenesis method. The modification may also include a chemical modification such as modification with a polymer such as polyethylene glycol.

Accordingly, the present invention further includes a gene variant encoding the above described protein analog.

In the description of the present invention, the recombinant DNA techniques used as conventional procedures can be performed as described in the literature Fristch et al., Molecular Cloning, Cold Spring Harbour Press (1989), unless otherwise indicated.

That is, the rice NADH-dependent reductase gene of the present invention can be obtained by, for example, preparing mRNA from rice anthers; synthesizing cDNA; and then screening the gene of interest from the obtained cDNA library.

Screening for the rice NADH-dependent reductase gene can be performed by, for example, preparing a probe and using this probe for plaque hybridization. The probe used for screening includes (i) an oligo DNA synthesized on the basis of part of the amino acid sequence in the protein of interest, (ii) a DNA fragment of a heterologous organism encoding the protein of interest, (iii) a DNA fragment confirmed to be homologous by random sequencing of the cDNA library, etc. In view of the bindability of the enzyme of the present invention to NADH, the coding region which has been demonstrated to be highly conserved in the NADH-dependent proteins (nucleotide numbers 52 to 123 shown in SEQ ID NO:1) may be synthesized and used as a probe. Alternatively, because this region has a homology of about 80% with the maize HC toxin reductase gene, DNA in a homologous or highly homologous region that corresponds to the protein coding region in the HC toxin reductase gene may be synthesized or such a region may be amplified by PCR (Polymerase chain reaction) method to use as a probe. It is also possible to isolate clones having a high homology with the already reported gene through the homology screening of gene sequences analyzed by the random sequencing of the rice anther cDNA library using GenBank data base (H. Uchimiya et al., Plant J., 2 (6), 1005–1009, 1992), then isolate clones containing a partial gene sequence having a homology with the maize HC toxin reductase and use this DNA fragment as a probe.

The cDNA library can be prepared by extracting mRNA from plant tissues such as calluses or anthers of rice, synthesizing cDNA therefrom with a template and a reverse transcriptase, and cloning the double-stranded cDNA resulting from polymerase reaction into a commercially available phage vector (λ ZAP™ II available from Stratagene) or a plasmid vector (pCD2, Okayama-Berg cDNA Library Synthesisis kit available from Toyobo Co., Ltd.) to transform it into E. coli or the like. Various cDNA library synthesis kits (such as ZAP-cDNA™ Synthesis kit available from Stratagene) may be used. A number of commercially available vectors may be used for preparing the library. Furthermore, the cDNA library may be screened by plaque hybridization or the like using, as a probe, a partial DNA fragment obtained as above by cDNA random sequencing in order to select clones carrying DNA which are complementary to the probe, prepare DNA from the clones, and analyze it in detail so that cDNA clones containing a full-length gene for the rice NADH-dependent reductase can be obtained. For the analysis of the cloned cDNA, the dideoxy method (Sanger F., J. Mol. Biol. 94, 441 (1975)) or the like can be used to determine the base sequence, or alternatively commercially available kits (Sequencing high kit available from Toyobo Co., Ltd.) or fluorescence sequencer (ABI PRISM™ DNA sequencer available from Applied Biosystems) may be used as well. The present invention is not limited to specific plant tissues as materials for constructing a cDNA library and similarly to methods for the construction.

The isolated rice NADH-dependent reductase gene, which contains a full length, can be produced in microorganisms such as *E. coli* by ligating it to a promoter such as tac promoter (Amann et al., Gene 40, 183 (1985)) or P1 promoter (Rosenberg M. et al., Methods Enzymol. 101, 123 (1983)), and thus the intended enzyme protein encoded by this gene can be obtained.

The enzyme protein of the present invention has a highly conserved region (nucleotide numbers 52 to 123 shown in SEQ ID NO:1) common in NADH-dependent proteins near the N-terminal, so that a partial protein deprived of this region, e.g. a protein obtained by expressing the C-terminal region resulting from digestion at the restriction endonuclease EcORV site (nucleotide numbers 426 shown in SEQ ID NO:1) or a synthetic peptide consisting of part of the amino acid sequence shown in SEQ ID NO:1 can be used as an antigen to prepare a highly specific antibody. Thus, all or part of the rice NADH-dependent reductase protein may be produced using a microorganism such as *E. coli* and then, the purified and isolated protein may be used as an antigen to prepare a polyclonal antibody or a monoclonal antibody by conventional procedures (CURRENT PROTOCOLS in MOLECULAR BIOLOGY, Ausubel et al., Current Protocols (1989)). The prepared antibody can be used in Western blotting, ELISA (Enzyme-Linked Immunosorbent Assay) or the like, which is based on antigen-antibody reactions, thereby readily examining the expression of the rice NADH-dependent reductase gene in rice plants.

The relationship between the isolated rice NADH-dependent reductase gene and the locus on the chromosome can be studied by gene mapping (S. R. McCouch, Biotechnology in Agriculture (C. B. Yuo et al., Kluwer Academic Publishers), 221–228, (1993)) using RFLP (Restriction Fragment Length Polymorphism). Chain analysis by Southern hybridization of the gene of the present invention using 100 or more RFLP markers as probes showed that the gene was mapped on the blast-resistant locus (Pi-i) of the 6th chromosome while existing in one copy on the rice chromosome.

Moreover, the gene encoding this rice NADH-dependent reductase can be ligated to a promoter such as 35S promoter derived from califlower mosaic virus (Guilley et al., Cell, 30, 763 (1982)) or a promoter for the ubiquitin gene derived from maize (Christensen et al., Plant Molecular Biology 18, 675 (1992)) to construct DNA or a vector capable of expressing the gene of the present invention, whereby an expression system in plants can be constructed. The constructed expression vector can be introduced into plants such as tobacco, tomato, lettuce, rice, barley, wheat, potato, maize, citrus, apple, grape, and turf glass by Agrobacterium method (Depicker et al., Mol. Gen. Gnet., 201, 477 (1985)), electropolation method (Toriyama et al., Bio/Technology, 6, 1072 (1988)), particle gun method (Klein et al., Nature, 372, 70 (1987)), or the like, so that increased amounts of the rice NADH-dependent reductase can be produced in vivo in the resulting transformed plants. As a result, the resistance to pathogenic microorganisms of plant diseases such as blast can be given to plants.

The present invention further provide a novel method for controlling a plant pathogenic microorganism, comprising protecting a plant from damages caused by the plant pathogenic microorganism by applying a plant transformed with an expression vector regulated to express rice NADH-dependent reductase in the plant to its cultivation. Although the method of the present invention can be applied to rice plants to protect the plants from blast, it should be understood that this method can also be applied to plants other than rice, e.g. any plants in which toxin produced by a pathogenic microorganism infecting the plants can be detoxified or inhibited by the rice NADH-dependent reductase. By the term "plant pathogenic microorganism(s)" is meant to include any plant pathogenic microorganisms capable of in vivo producing the toxin which is detoxified by the rice NADH-dependent reductase of the present invention.

According to the present invention, the gene encoding rice NADH-dependent reductase can be used to transform plants such as rice and remarkable advantages are offered for plant breeding, e.g. improved plant disease resistance and control of metabolic systems, by regulating a resistance reaction to plant diseases associated with the enzyme of the present invention in plant bodies.

The following examples illustrate the present invention, but are not intended to limit it.

EXAMPLES

Example 1

A. Isolation of Rice Anther mRNA and Synthesis of cDNA

About 1000 anthers of rice (*Oryza sativa* cv. Hayayuki) were frozen in liquid nitrogen and grounded in a mortar. They were added to 5 ml of a solution containing 100 mM LiCl, 100 mM Tris-HCl (pH 8.0), 10 mM EDTA and 1% SDS and 5 ml of phenol preheated at 80° C.; stirred; and then mixed with 5 ml of chloroform/isoamyl alcohol (volume ratio 24:1). After stirring, the mixture was centrifuged at 12000 rpm for 15 minutes to recover the supernatant. An equivalent amount of 4 M lithium chloride solution was added to the surpernatant and allowed to stand at −80° C. for one hour, then centrifuged to recover the precipitate. The precipitate was dissolved into 1 ml of sterilized water and then mixed with 100 $\mu$l of 3 M sodium acetate solution and 2 ml of ethanol, and the mixed solution was allowed to stand at −80° C. overnight and centrifuged to recover the total RNA as precipitate. The precipitate was dissolved in 500 $\mu$l of a RNA lysis solution containing 10 mM Tris-HCl (pH 8.0), 1 mM EDTA, 0.1% SDS and mixed with 100 $\mu$l of oligo (dT) cellulose (Pharmacia), and the mixed solution was allowed to stand at 65° C. for 5 minutes and then rapidly cooled on ice and further mixed with 60 $\mu$l of 5 M NaCl. The mixture was allowed to stand at room temperature for 10 minutes and then centrifuged to recover the precipitate. To the precipitate was added 500 $\mu$l of the RNA lysis solution followed by centrifugation at 65° C. for 5 minutes to recover the supernatant. The supernatant was mixed with 50 $\mu$l of 3 M sodium acetate and 1 ml of ethanol, and the mixture was allowed to stand at −80° C. for one hour, then centrifuged to recover about 2 μg of mRNA. The mRNA was dissolved in 10 μl of sterilized water and 5 μl of an aliquot thereof was used for cDNA synthesis. The cDNA synthesis was performed by synthesizing a first strand cDNA and a second strand cDNA using ZAP-cDNA synthesis kit (Toyobo Co., Ltd.), blunt-ending the cDNAs, ligating them with an EcoRI adapter, cleaving the cDNAs with the restriction endonuclease XhoI, ligating them to Uni-ZAP™ XR vector (Stratagene) before packaging, and then infecting E. coli PLK-F' with the package to prepare a cDNA library.

B. Preparation of a DNA Probe

E. coli strain XL-1 Blue was infected with the phage cDNA library prepared from rice anthers to form colonies carrying a plasmid containing cDNA in a pBluescript SK(−) plasmid vector (Stratagene) by in vitro excision, and the plasmid DNA was extracted from the cells cultured in 5 ml of LB medium. Each cDNA clone was randomly sequenced by a fluorescence sequencer (Applied Biosystems) to give a cDNA clone containing about 650 bp downstream of the nucleotide number 603 shown in SEQ ID NO:1 (designated as YK756). The DNA base sequence of about 300 bp at the 5' end of this cDNA fragment showed a homology of about 78% with the gene sequence of maize HC toxin reductase. The plasmid DNA of this clone was digested with the restriction endonuclease EcoRI, and a DNA fragment of about 650 bp was recovered by agarose gel electrophoresis and labeled by using a DIG DNA labelling kit (Boehringer Mannheim) to yield a probe.

C. Screening of the cDNA Library

In order to obtain a full-length cDNA containing about 600 bp upstream of the 5' end, the cDNA library was screened by plaque hybridization using the DNA fragment prepared from YK756 clone as a probe. The E. coli strain XL-1 Blue was infected with the phage cDNA library prepared from rice anthers to form about 100,000 plaques on a plate, which was covered with a nylon membrane Hybond N+ (Amersham) and allowed to stand for one minute. Then, this membrane was denatured with a solution of 0.5 M NaOH, 1.5 M NaCl, naturalized with a solution of 0.5 M Tris-HCl (pH 7.2), 1.5 M NaCl, washed with 2×SSC (0.3 M NaCl, 0.03 M sodium citrate), and then dried. This membrane was allowed to stand in a hybridization solution at 42° C. for one hour and slowly shaken at 42° C. overnight in an exchanged hybridization solution containing a probe labeled with DIG (i.e. Digoxigenin available from Boehringer Mannheim). This membrane was washed twice in 2×SSC, 0.1% SDS at room temperature for 5 minutes, then twice in 0.1×SSC, 0.1% SDS at 68° C. for 15 minutes. This membrane was tested by a DIG fluorescence detection kit (Boehringer Mannheim) to detect positive clones. Six positive clones were obtained from about 400×10⁴ recombinants. From these clones were obtained plasmide vectors by in vitro excision, and then the plasmid DNA from each clone was extracted. The plasmid DNA was cleaved with the restriction endonuclease EcoRI and the inserted cDNA was assesed by agarose gel electrophoresis in order to obtain a cDNA clone YK1 containing a DNA fragment of about 1200 bp at maximum.

D. Sequence of the cDNA Clone

The cloned cDNA was cleaved with the restriction endonuclease SacI into two DNA fragments which were subsequently subcloned into pBluescript SK(−) vector. The DNA fragment of about 700 bp at the 5' side was cleaved with the restriction endonucleases EcoRV and XhoI to give smaller fragments, which were then subcloned into pBluescript SK(−). The DNA fragment of about 700 bp at the 3' side was separately cleaved with the restriction endonuclease PstI to give smaller fragments, which were then subcloned into pBluescript SK(−). Thus obtained clones were sequenced by Sequencing High Kit (Toyobo Co., Ltd.) with T7 and T3 primers (both available from Toyobo Co., Ltd.) in order to determine the base sequence. The resulting base sequence is shown in SEQ ID NO:1 in the SEQUENCE LISTING. The deduced amino acid sequence of the rice NADH-dependent reductase (1–363) is also shown in SEQ ID NO:1.

E. Analysis of the Base and Amino Acid Sequences

Analysis of the DNA and amino acid sequences of the rice NADH-dependent reduactase by SDC-GENETYX (SDC Software Development) indicated that they were homologous only to those of the already isolated maize HC toxin reductase with about 80% of homology at genetic level and about 73% of homology at amino acid level. There exists a conserved sequence at the NADH-binding site near the N-terminal of the protein and this region shows a homology with other NADH-dependent dihydrofrabonol-4-reductases from for example petunia, indicating that the protein of the present invention has NADH as coenzyme. As a result of linkage analysis by Southern hybridization using RFLP markers, the rice NADH-dependent reductase gene was mapped at the Pi-i locus on the 6th chromosome, showing that this gene was one of blast-resistant loci, Pi-I, and exists in one copy on the chromosome.

Example 2

Expression of the Rice NADH-Dependent Reductase Gene in E. coli and purification of the Expressed Protein The cDNA clone obtained was digested with the restriction endonuclease EcoRI and recovered as a DNA fragment of about 1.3 Kb containing a protein translational region. Then, the fragment was inserted into the expression vector pGEX2T (Pharmacia) at the restriction endonuclease EcoRI site in E. coli so that a fusion protein with glutathione-S-transferase was expressed. The E. coli strain JM109 was transformed with the constructed vector and cultured in LB medium containing 50 ppm ampicilin for 15 hours. After induction with 1 MM IPTG (isopropyl-β-thiogalactoside), a YK1 fusion protein was expressed. The cell culture was disrupted by sonication in 1×PBS buffer, followed by centrifugation to recover the supernatant. The fusion protein in the supernatant was adsorbed on a glutathione Sepharose column (Pharmacia) and subjected to SDS-PAGE electrophoresis, thereby showing a molecular weight of about 60,000 daltons.

The fusion protein adsorbed on the glutathione Sepharose column was cleaved with thrombin in a thrombin cleavage solution (50 mM Tris-HCl (pH 7.5), 150 mM NaCl, 2.5 mM CaCl$_2$) to release YK1 protein from the column, which protein had a molecular weight of about 40,000 daltons as determined by SDS-PAGE, almost identical with the value of 39234 daltons calculated from the amino acid sequence deduced from the gene sequence. About 5 mg of YK1 protein was recovered from about 7 liters of the cell culture.

Further, the bindability of crude YK1 protein to NADH was examined by using Blue Cellulofine (Biochemical Industries) consisting of Cibacron Blue 3G-A fixed on a Cellulofine column. 4.7 mg of YK1 protein dissolved in 8 ml of 50 mM Tris-HCl (pH 8.0) solution was applied to 10 ml of a Blue Cellulofine column (φ10 mm×125 mm), washed with 100 ml of the same solution, then eluted with 50 ml of an eluent containing 5 mM NAD to recover eluate fractions (Fraction Nos. 1 to 10) by fractionating the eluate in a volume of 5 ml. The analysis of the protein content and SDS-PAGE electrophoretic pattern of each eluate fraction showed that YK1 protein was eluted in fraction No. 3 to No.

6 to give 2.2 mg of homogeneous YK1 protein. The recovery was 47%. The purified rice NADH-dependent reductase protein as an antigen was injected in a rabbit in order to obtain antibodies thereto from the serum of the rabbit. YK1 protein adsorbed on the Blue Sepharose column was specifically eluted with NAD, indicating that YK1 protein had an ability to bind to the coenzyme NAD, i.e. to catalyze a reaction involving a nicotinamide dinucleotide compound such as NAD as coenzyme.

Example 3
Construction of an Expression Vector in Plant Cells

An expression vector was prepared by the procedures set forth below according to the construction scheme shown in FIG. 1.

The restriction endonuclease Hind III site downstream of the 3' of the cDNA clone YK1 obtained in Example 1C was cleaved, and then blunt-ended with Klenow enzyme in the presence of four dNTPs, and a BamHI linker (Toyobo Co., Ltd.) was inserted into the product. After this plasmid with BamHI site substituted for HindIII site was further cleaved with BamHI to isolate a cDNA fragment containing full-length YK1, the cDNA fragment was inserted into the BamHI site downstream of a ubiquitin promoter of the plant expression vector pAHC17. The constructed expression vector was under the control of the ubiquitin promoter, and could be transformed into plants such as rice by using electropolation, polyethylene glycol, particle gun or other methods in order to express rice NADH-dependent reductase.

Figure 1:
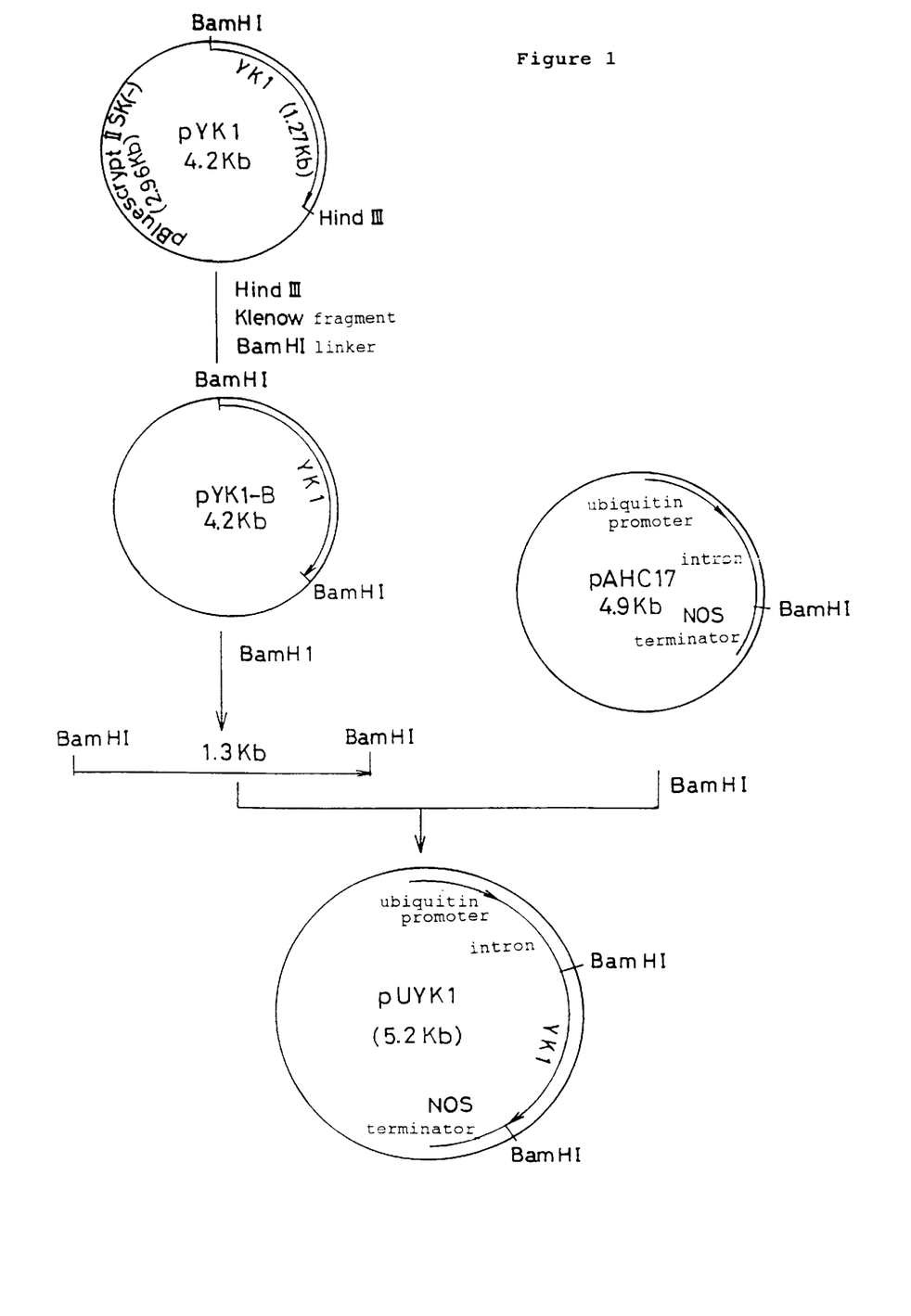

The starting vector pYK1 of FIG. 1 containing the gene of the present invention was transferred into an E. coli strain (Escherichia coli strain HB101) and deposited on Dec. 18, 1995 with the National Institute of Bioscience and Human-Technology of the Agency of Industrial Science and Technology of the Ministry of International Trade and Industry (1-1-3, Higashi, Tsukuba-city, Ibaraki-prefecture, Japan) in terms of the Budapest Treaty under the Accession No. FERM BP-5340.

Example 4
Transformation into Rice

The expression vector obtained in Example 3 was introduced into protoplasts of rice by electropolation (Toriyama et al., Bio/Technology, 6, 1072 (1988)).

Calluses were derived from rice mature seeds on IN medium and subcultured every one week on AA liquid medium, and then treated with an enzyme solution (0.05% Pectolyase Y-23, 2% Cellulase ONOZUKA RS, 0.01% calcium chloride, 0.36 M mannitol) (Ohtsuki et al., Breeding 38 (Suppl. 1) 78 (1988)) for two hours to isolate rice propoplasts. This solution was filtered through a nylon filter of 200 meshes, then centrifuged at 100×g for four minutes to recover protoplasts as precipitate. The protoplasts were washed twice with 0.45 M mannitol, 0.1 mM calcium chloride solution, then suspended in the same solution to a concentration of 1×10⁶ protoplasts/ml. After plasmids (10 μ g each of the expression vector for YK1 and the expression vector for hygromycin-resistant gene (pCH, Matsuki et al., Mol. Gen, Genet., 220, 12, (1989))) were added to 1 ml of the protoplast suspension, the suspension was cooled on ice for 5 minutes. This solution was exposed to electric pulses of 800 μF, 300 V by using an electropolation apparatus (BRL, Cell-Porator™), and left in ice for 5 minutes. After centrifugation at 100×g for 4 minutes, protoplasts were recovered as precipitate and suspended in 1 ml of AAS medium. The suspension was thoroughly mixed with 1 ml of AAS medium containing 0.8% agarose (LO-3 available from Takara Shuzo) dissolved and maintained at 50° C. The mixture was transferred to a 6 cm petri dish in which the agarose was then solidified. Thereafter, the agarose was transferred to a 9 cm petri dish and incubated with 5 ml of AAS medium in which about 0.5 g of rice liquid-cultivated calluses were suspended as nurse cells, while shaking at 50 rpm at 25° C. in the dark. After one week, the nurse cells were washed off and the agarose containing propoplasts was transferred to a flesh 9 cm petri dish and continually incubated with AAS medium replaced by GR medium every one week to gradually lower the osmosis due to the high level sucrose so that AAS medium was completely replaced by GR medium in four weeks. After two weeks, 30 μg/ml of hygromycin (Sigma) was added to the medium to select transformed calluses. Ten to several tens of hygromycin-resistant calluses were obtained per dish, plated onto TI medium and cultured under fluorescent lamp at 25° C. to give hygromycin-resistant redifferentiated plants. The obtained plants were acclimatized and then transplanted into soil.

The compositions of the media used above were based on the description in "Plant gene manipulation manual—How to produce transgenic plants" by H. UCHIMIYA, Kodansha Scientific, Tokyo, Japan (1990), among which IN, AAS, GR and TI media have the following compositions.

IN medium: MS medium supplemented with 2 mg/l of 2,4-dichlorophenoxyacetic acid (2,4-D) and 30 g/l of agarose;

AAS medium: AA medium free from kinetin and gibberellin (GA3) and supplemented with 120 g/l of sucrose;

GR medium: N6 medium supplemented with 1 g/l of proline, 0.3 g/l of casein hydrolysate, 60 g/l of sucrose, 1 mg/l of 2,4-D;

TI medium: N6 medium supplemented with 0.01 mg/l of naphthaleneacetic acid, 0.1 mg/l of benzyladenine, 40 g/l of sucrose, 10 g/l of agarose type I (Sigma).

Example 5
Detection of the Transferred Gene by PCR Method

DNA was extracted from the obtained plants according to the method of McGarxey et al. (BioTechniques, (1991), vol. 11 (4), 428–432), amplified by PCR method using synthetic oligomers (5'AGTACGGGGTTGGTGCTCTCGC3', 5'ATCTCCACTGACGTAAGGGATGAC3') (SEQ ID NO:3 and 4) and subjected to agarose gel electrophoresis to confirm that the hygromycin-resistant gene had been introduced. Similarly, the DNA was amplified by PCR method using synthetic oligomers (5' TCATCGCAAGACCGGCAACAG3', 5'CCGGGAGTTCGAGGTGGTCA3') (SEQ ID NO:5 and 6) and subjected to agarose gel electrophoresis to demonstrate that the YK1 gene had been introduced together with the hygromycin-resistant gene into 9 individuals in 5 of 11 cell lines.

Example 6
Expression Analysis of YK1 Protein in Plants Transformed with the YK1 Gene The expression of YK1 protein in plants transformed with the YK1 gene was analyzed by Western blotting method. After about 100 mg of leaf was triturated with 100 μl of PBS buffer and centrifuged at 15,000 rpm for 5 minutes, the supernatant was recovered. The protein was quantitated by a method using Coomassie Brilliant Blue G-250 (Bio-Rad), then about 20 μg of crude extracted protein was electrophoresed on SDS-polyacrylamide gel. After electroblotted to a PVDF membrane (MILLIPORE), the membrane was reacted with an antibody prepared using a rabbit and then with a peroxidase-labeled secondary antibody, and detection was performed using 4-chloronaphthol as a substrate. As a result, YK1 protein could be detected as a band at about 40,000 daltons almost equal to the presumed molecular weight, and the increase in expression level was observed in 4 of 9 individuals. No increase in expression level could be observed in the other 5 individuals.

Example 7

Inoculation Test of a Blast Pathogen into the Gene-Transferreded Plants

A suspension of spores of a blast pathogenic microorganism (*Pyricularia oryzae*) (2×10⁵ spores/ml) was mixed with an appropriate amount of a surfactant (NITTEN TR available from Nissan Chemical Industries) and sprayed with a hand sprayer on the plants transformed with the YK1 gene and with plants as control redifferentiated from protoplasts. These plants were kept under the conditions of 25° C. and humidity of 100% for 24 hours. Then, cultivation was continued at 22° C. and the plants were tested 8 days after inoculation. As a result, many lesions were observed in the control plants, but the transformed plants into which the YK1 gene had been introduced and YK1 protein had been expressed had no formation of any lesion, thus showing the resistance to *Pyricularia oryzae*. This revealed that the expression of the gene of the present invention in plants could give a resistance to plant pathogenic microorganisms such as *Pyricularia oryzae*, whereby the plants could be protected from damages caused by the pathogens.

What is claimed is:

1. An isolated rice NADH-dependent reductase gene.

2. The gene of claim 1, comprising a base sequence encoding the amino sequence of SEQ ID NO: 2.

3. The gene of claim 1, wherein said base sequence comprises nucleotide 10 to nucleotide 1098 of SEQ ID NO:1.

4. An isolated DNA comprising the rice NADH-dependent reductase gene of claim 1 and capable of being expressed in microorganism or plant cells.

5. An expression vector comprising the rice NADH-dependent reductase gene of claim 1 and capable of expressing the rice NADH-dependent reductase gene in microorganism or plant cells.

6. A plant transformed with the expression vector of claim 5.

7. The transformed plant of claim 6 which is selected from the group consisting of tobacco, tomato, lettuce, rice, barley, wheat, potato, maize, citrus, apple, grape, and turf grass.

8. A seed obtained from the plant of claim 6.

9. A method for protecting plants from damage caused by a plant pathogenic fungus, comprising transforming a plant with the expression vector of claim 6.

10. The method of claim 9, wherein said plant pathogenic microorganism is a rice blast pathogen.

11. The method of claim 9, wherein the plant pathogenic fungus is *Pyricularia oryzae*.

12. The method of claim 11, wherein the selected from the group consisting of tobacco, tomato, lettuce, rice, barley, wheat, potato, maize, citrus, apple, grape, and turf grass.

13. A method of producing a rice NADH-dependent reductase, comprising transforming a microorganism with the expression vector of claim 5, culturing the transformed microorganism to produce the reductase, and isolating the reductase.

14. The method of claim 13, wherein the microorganism is *E. coli*.

* * * * *